United States Patent
Sankey

Patent Number: 5,863,363
Date of Patent: Jan. 26, 1999

[54] METHOD OF MAKING AN ARTIFICIAL EYE

[76] Inventor: Gregory Sankey, 10212 5th Ave. NE. #210, Seattle, Wash. 98125

[21] Appl. No.: 889,623

[22] Filed: Jul. 8, 1997

Related U.S. Application Data

[62] Division of Ser. No. 713,119, Sep. 16, 1996, Pat. No. 5,733,333.

[51] Int. Cl.$^6$ ..................................................... B29D 11/00
[52] U.S. Cl. ............................................. 156/61; 264/1.7
[58] Field of Search ...................... 264/1.1, 1.7; 156/61; 623/4, 6

[56] References Cited

U.S. PATENT DOCUMENTS

| | | | |
|---|---|---|---|
| 2,483,832 | 10/1949 | Kingston | 623/4 |
| 2,603,792 | 7/1952 | Jardon et al. | 623/4 |
| 2,675,561 | 4/1954 | Clarke | 623/4 |

*Primary Examiner*—Mathieu D. Vargot
*Attorney, Agent, or Firm*—Michael J. Tavella

[57] ABSTRACT

A device and method for making artificial eyes. The device uses either photographs of a patient's eye, or, the patient's eye is digitally scanned. This digital image can then be read, manipulated and changed on a computer screen using common software. Once the image is perfected, it can be printed with a color laser printer. The image (either a digital printout or photograph) can then be cut and attached to an iris button. To prevent smearing of the image during the curing, a formed bonnet is placed between the iris button and the cornea. This bonnet absorbs the compression of the cornea during curing, thereby preventing smearing of the image.

8 Claims, 4 Drawing Sheets

METHOD OF MAKING AN ARTIFICIAL EYE

This application is a continuation of application Ser. No. 08/713,119, filed Sep. 16, 1996, now U.S. Pat. No. 5,733,333.

This invention relates to artificial eyes and particularly to artificial eyes using digitally scanned irises and pressure relieving elements during the construction thereof.

BACKGROUND OF THE INVENTION

Artificial eyes have seen little change over the years. Originally made from glass, craftspersons began using synthetic materials during World War II. Since then, the basic method of making artificial eyes has remained the same. Since the 1950's, materials such as methyl methacrylate have been used to make the artificial eyes. An example of this type of eye can be found in U.S. Pat. No. 2,551,781. Typically, an artificial eye is made in steps: the body of the eye is formed; a colored iris is painted on, or other wise attached to a flat-surfaced "button"; the iris button is attached to the body of the eye; and then an artificial cornea is sealed over the assembly.

The most difficult part of making an artificial eye is the iris. Humans have multicolored irises that can vary significantly. To achieve realistic color matching, the iris is typically painted onto the iris button. This is painstaking work that involves considerable artistic skill. Several U.S. patents discuss using photographs in lieu of painting the iris. In this technique, a photograph can be taken of a person's remaining eye and the iris can be developed from that photograph, cut, and attached to an iris button. Examples of this technique are found in U.S. Pat. Nos. 2,580,583, 2,603,791, 2,603,792, and 5,026,392. Although these patents teach using photographs to color the irises, two problems exist that have prevented extensive use of photographs for irises. First, although photographs can accurately depict the color of a human iris, when the photograph is placed under the artificial cornea, the colors are sometimes distorted. As a result, complex developing techniques must be used to develop the photographs to correct for this distortion before the cornea is installed. Obviously, this may require several tries before a close match is reached. Such experimentation is expensive and, therefore, is limited in usefulness.

The second problem is more difficult. To complete the formation of an artificial eye, the cornea is fastened to the eye body using adhesives that have strong solvents. Moreover, the adhesive must be cured while the cornea is under pressure. A small clamp vice is used for this part of the process. The solvents are strong enough to dissolve the photographic image of the iris that is attached to the iris button. In its softened state, the photographic image is susceptible to smearing as the cornea is being compressed by the clamp vice. Obviously, only a slight amount of smearing is enough to ruin the artificial eye, thereby requiring the maker to begin again.

For these two primary reasons, the use of photographs for irises in artificial eyes has remained more theory than practice.

SUMMARY OF THE INVENTION

The instant invention overcomes these two problems. First, instead of ordinary photographs (which still may be used in this technique), the patient's eye is digitally scanned. This digital image can then be read, manipulated and changed on a computer screen using common software. Once the image is perfected, it can be printed with a color laser printer. This image can then be cut and attached to an iris button. To prevent smearing of the image during the curing, a formed bonnet is placed between the iris button and the cornea. This bonnet absorbs the compression of the cornea during curing, thereby preventing smearing of the image.

It is an object of this invention to produce an artificial eye that uses a photographic or printed iris that is not smeared in processing.

It is a further object of this invention to produce an artificial eye that uses digital photographic techniques and computer enhancement to provide a printed iris that is corrected to distortions caused by the artificial cornea.

It is yet a further object of this invention to produce a method of making artificial eyes that is uniform and consistent can be performed using lower skilled technicians.

DETAILED DESCRIPTION OF THE INVENTION

Figure 1:
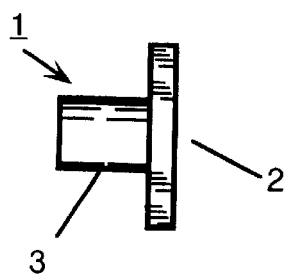
FIG. 1 is a side view of a typical iris button.
Figure 2:
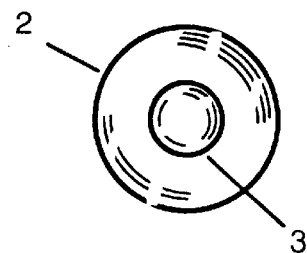
FIG. 2 is a front view of a typical iris button.
Figure 3:
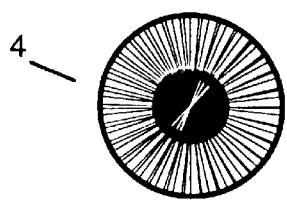
FIG. 3 is a front view of a colored iris sheet.
Figure 4:
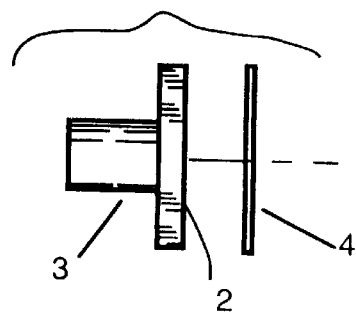
FIG. 4 is an exploded view of an iris button with an iris sheet ready for mounting.

Referring now to FIGS. 1–6, details of the basic iris construction are shown. FIG. 1 shows a typical iris button 1. The iris button 1 has a flat mounting surface 2 (see FIG. 2) and a post 3 for mounting the iris in the final eye assembly. FIG. 3 shows a typical iris 4. This iris can be hand painted on the iris button's 1 flat surface 2. Alternatively, photographs or digital color printouts of an iris 4 (see discussion below and FIGS. 12–14) can also be used. FIG. 4 shows the placement of the iris 4 on the mounting surface 2 of the iris button 1. If the iris 4 is a photograph or printout, the iris 4 is glued to the mounting surface 2 of the iris button 1.

Figure 5:
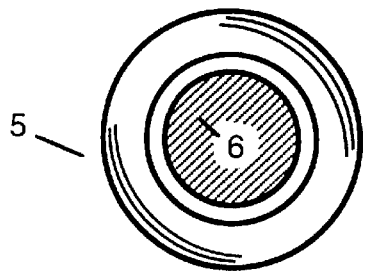
FIG. 5 is a top view of a bonnet cover.
Figure 6:
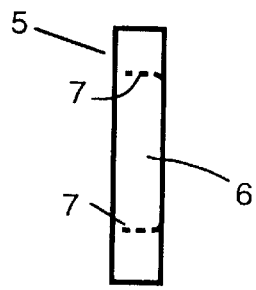
FIG. 6 is a side view of the bonnet cover.
Figure 7:
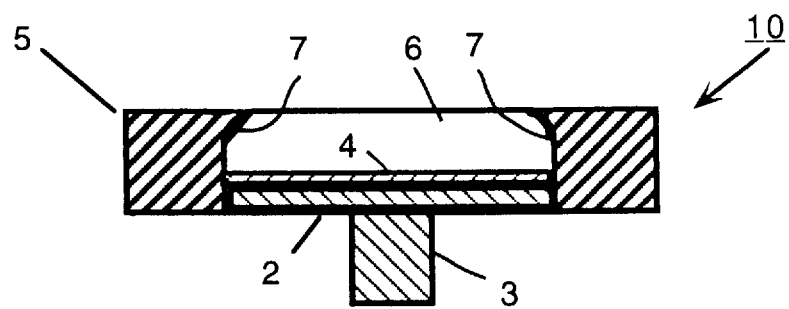
FIG. 7 is a cross-sectional view of the mounted iris button placed in the bonnet cover.

FIG. 5 is a top view of the bonnet 5. FIG. 6 is a cross sectional view of the bonnet 5. The bonnet 5 has an open center 6 that is framed by an annular side wall 7. The open center 6 of the bonnet 5 is designed to receive the iris 4 and iris button 1 as assembled. FIG. 7 shows the placement of the iris button 1 within the bonnet 5. This forms a bonnet-iris assembly 10.

Figure 8:
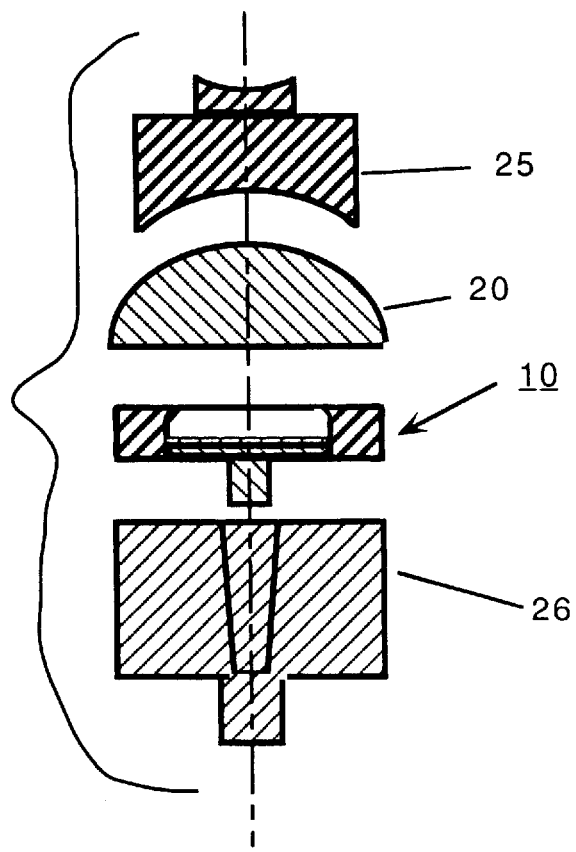
FIG. 8 is an exploded view of an iris-cornea system for placement in a set of compression jaws.
Figure 9:
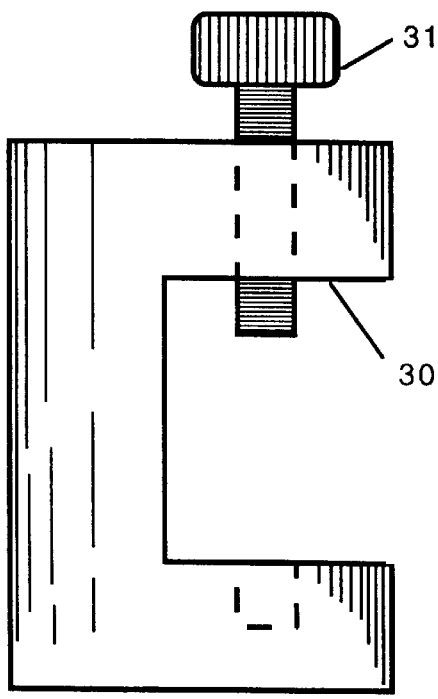
FIG. 9 is a side view of a compression vice.
Figure 10:
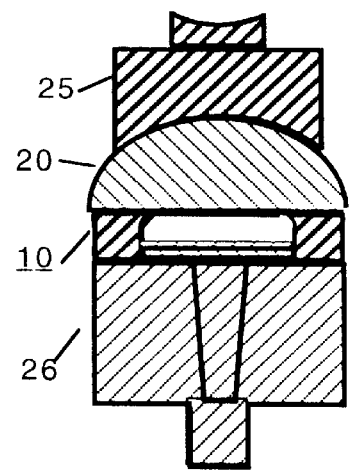
FIG. 10 is a cross-sectional view of the artificial eye components in the compression jaws as assembled.
Figure 11:
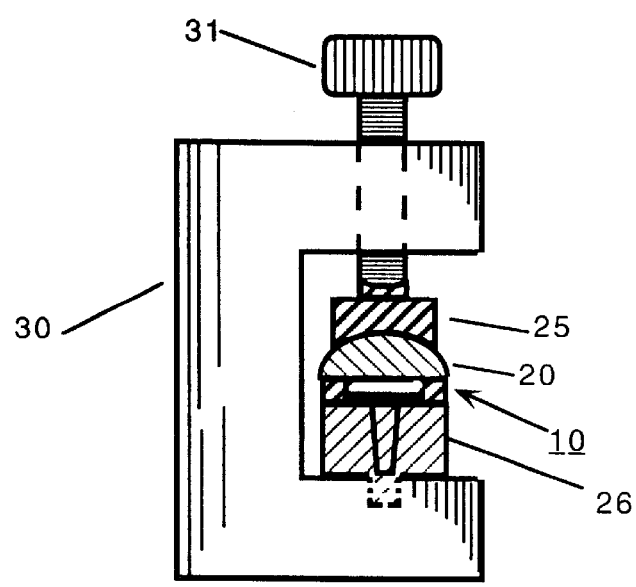
FIG. 11 is a side view of the assembled components assembled in the compression vice for curing.

Referring now to FIG. 8, the bonnet-iris assembly 10 is attached to an artificial cornea 20 using a pressure vice 30 and adhesives. The cornea 20 and bonnet-iris assembly 10 are held in clamps 25 and 26. FIG. 8 shows the cornea 20 and bonnet-iris assembly 10 and the clamps 25 and 26 in an exploded view. FIG. 9 is a side view of the vise 30. FIG. 10 is a side view of the eye assembly ready for installation in the vice 30. FIG. 11 shows the assembly mounted in the vice 30 being cured. Once the cornea 20 and bonnet-iris assembly 10 and the clamps 25 and 26 are placed in the vice 30, thumb screw 31 is tightened down over the assembly, causing the parts to be squeezed. Without the bonnet is it possible for the cornea 20 to slide over the iris 4; when this happens, the iris often smears. The bonnet 5 secures the iris 4 and prevents the ink or photochemical from smearing during the cure process. After the parts are cured, the components are removed from the vice 30 and the clamps 25 and 26 are removed. This process ensures an iris that is relatively perfect. Moreover, this technique produces realistic artificial eyes on a uniform basis even under mass production by lower skilled technicians.

Figure 12:
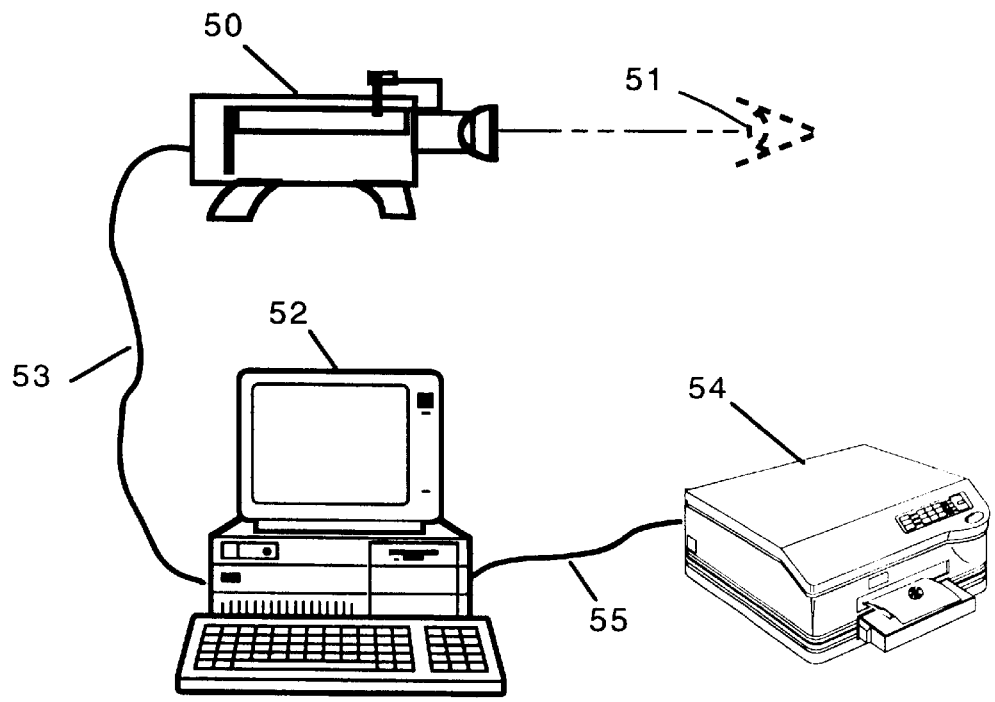
FIG. 12 is a detail view of a digital camera-computer system for capturing a patient's true iris color.
Figure 13:
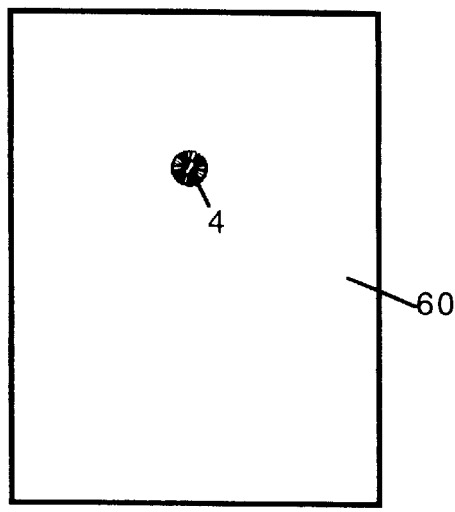
FIG. 13 is a detail view of a printout from the digital camera-computer system showing an iris print.
Figure 14:
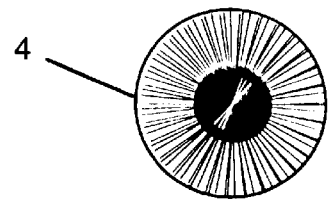
FIG. 14 is an enlarged view of the iris print, ready for mounting as cur from the printout. This view is the same view as FIG. 3.

FIGS. 12–14 show details of the system for producing digital color renditions of irises using computers. FIG. 12 shows the basic components of the system. A digital camera 50 (either video or still) captures the image of a patient's iris 51. This image is then transmitted to a computer 52 through cables 53 or other means know to the art. The computer, running common drawing programs such as PHOTO SHOP sold by Adobe, COREL DRAW, AND PHOTOSTYLER, can work the image and adjust the color as needed based on development factors arising from the making of the eye itself. The two biggest adjustments are caused by the natural distortion caused by the plastic cornea. These are a lightening of the color, which requires the color to be darkened and the geometric distortion, which magnifies the iris approximately 0.5 mm. The software can be used to compensate for this magnification of the iris. When the iris is finished, it can be printed on a laser printer 54 that is fed by cable 55.

FIG. 13 shows a typical color printout 60 showing the iris 4 (note that the iris is not in proper proportion to the paper; it is enlarged for detail). FIG. 14 shows an enlarged view of the iris cut from the printout 60, ready for mounting using the techniques and methods described above.

The present disclosure should not be construed in any limited sense other than that limited by the scope of the claims having regard to the teachings herein and the prior art being apparent with the preferred form of the invention disclosed herein and which reveals details of structure of a preferred form necessary for a better understanding of the invention and may be subject to change by skilled persons within the scope of the invention without departing from the concept thereof.

I claim:

1. The method of forming an artificial eye comprising the steps of:
   a) creating an artificial iris;
   b) attaching said artificial iris to the top of an iris button, thereby forming an iris assembly;
   c) placing said iris assembly into a bonnet, thereby forming a bonnet-iris assembly; and
   d) attaching an artificial cornea to said bonnet-iris assembly.

2. The method of forming an artificial eye of claim 1 further comprising the steps of adding adhesive to the bonnet-iris assembly and curing the adhesive while holding the artificial cornea and bonnet-iris assembly in a vise.

3. The method of forming an artificial eye of claim 1 wherein the step of creating an iris comprises photographing an iris.

4. The method of forming an artificial eye of claim 1 wherein the step of creating an iris comprises producing a digital image of an iris.

5. The method of forming an artificial eye of claim 4 further comprising the steps of:
   a) using a digital camera to capture an image of an iris;
   b) adjusting the image in a computer; and
   c) printing said image through a printing means.

6. The method of forming an artificial eye of claim 5 wherein the printing means is a color laser printer.

7. The method of forming an artificial eye of claim 5 wherein the step of adjusting the image comprises the step of darkening the color of the iris to compensate for the natural lightening of the iris color caused by the artificial cornea.

8. The method of forming an artificial eye of claim 5 wherein the step of adjusting the image comprises the step of compensating for a natural magnification of the iris caused by the artificial cornea.

\* \* \* \* \*